United States Patent [19]

Giersch

[11] 4,344,531
[45] Aug. 17, 1982

[54] HEMOSTATIC CLIP CARTRIDGE

[75] Inventor: Robert V. C. Giersch, Raleigh, N.C.

[73] Assignee: Edward Weck & Company, Inc., Research Triangle Park, N.C.

[21] Appl. No.: 185,095

[22] Filed: Sep. 8, 1980

[51] Int. Cl.³ .................... B65D 83/00; B65D 85/24; B65D 85/62
[52] U.S. Cl. .................................. 206/339; 206/340
[58] Field of Search ............... 206/339, 340, 338, 345; 72/424, 410; 227/143

[56] References Cited

U.S. PATENT DOCUMENTS

| 2,758,302 | 8/1956 | White | 206/339 |
| 3,278,107 | 10/1966 | Rygg | 206/340 |
| 4,050,578 | 9/1977 | Eckert | 206/340 |

Primary Examiner—Joseph Man-Fu Moy
Attorney, Agent, or Firm—Lawrence S. Levinson; John J. Archer

[57] ABSTRACT

A hemostatic clip cartridge is formed of a base and cover to contain a plurality of pre-formed U-shaped hemostatic clips in a column which is spring-biased to move along a track in the base and toward a delivery station which is shaped to make individual clips available to a hand held forceps type clip applier.

4 Claims, 8 Drawing Figures

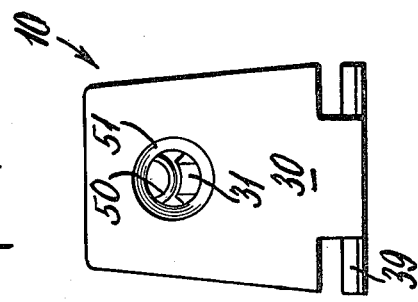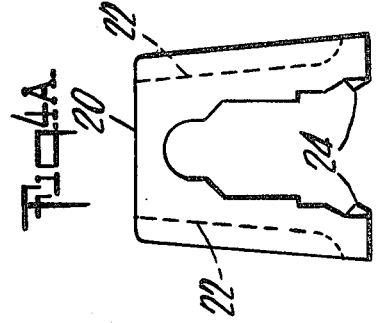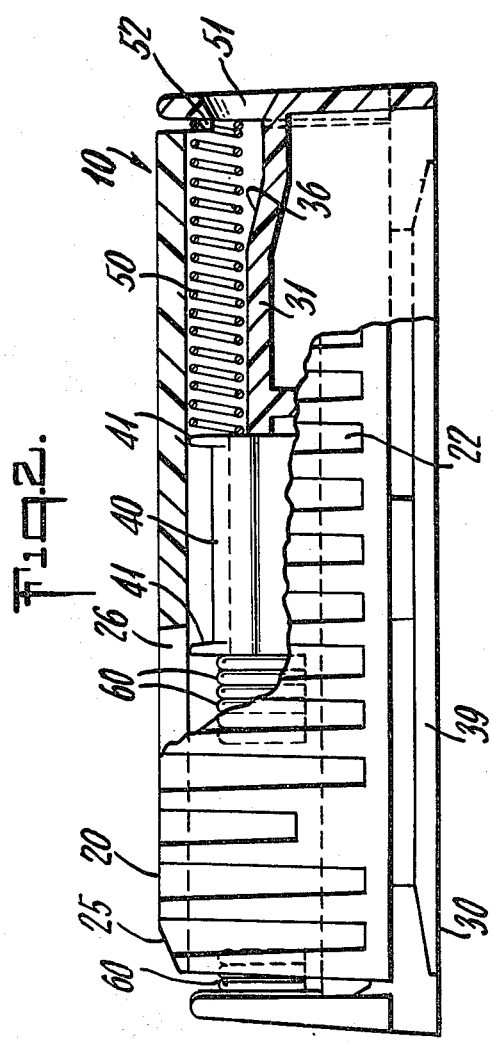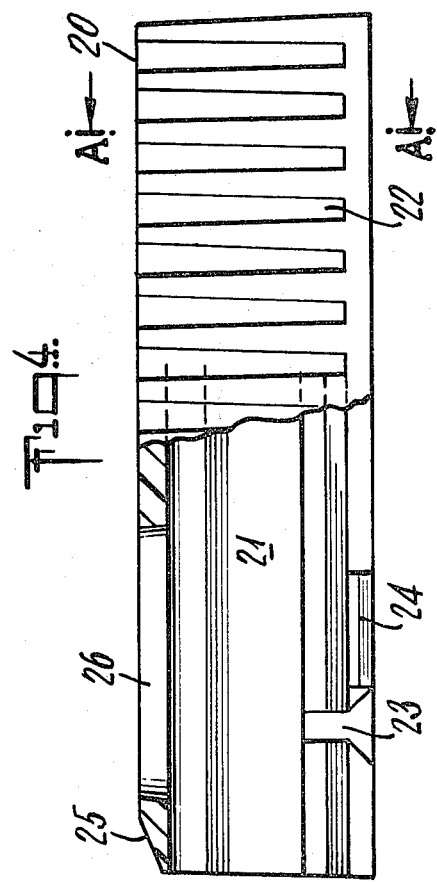

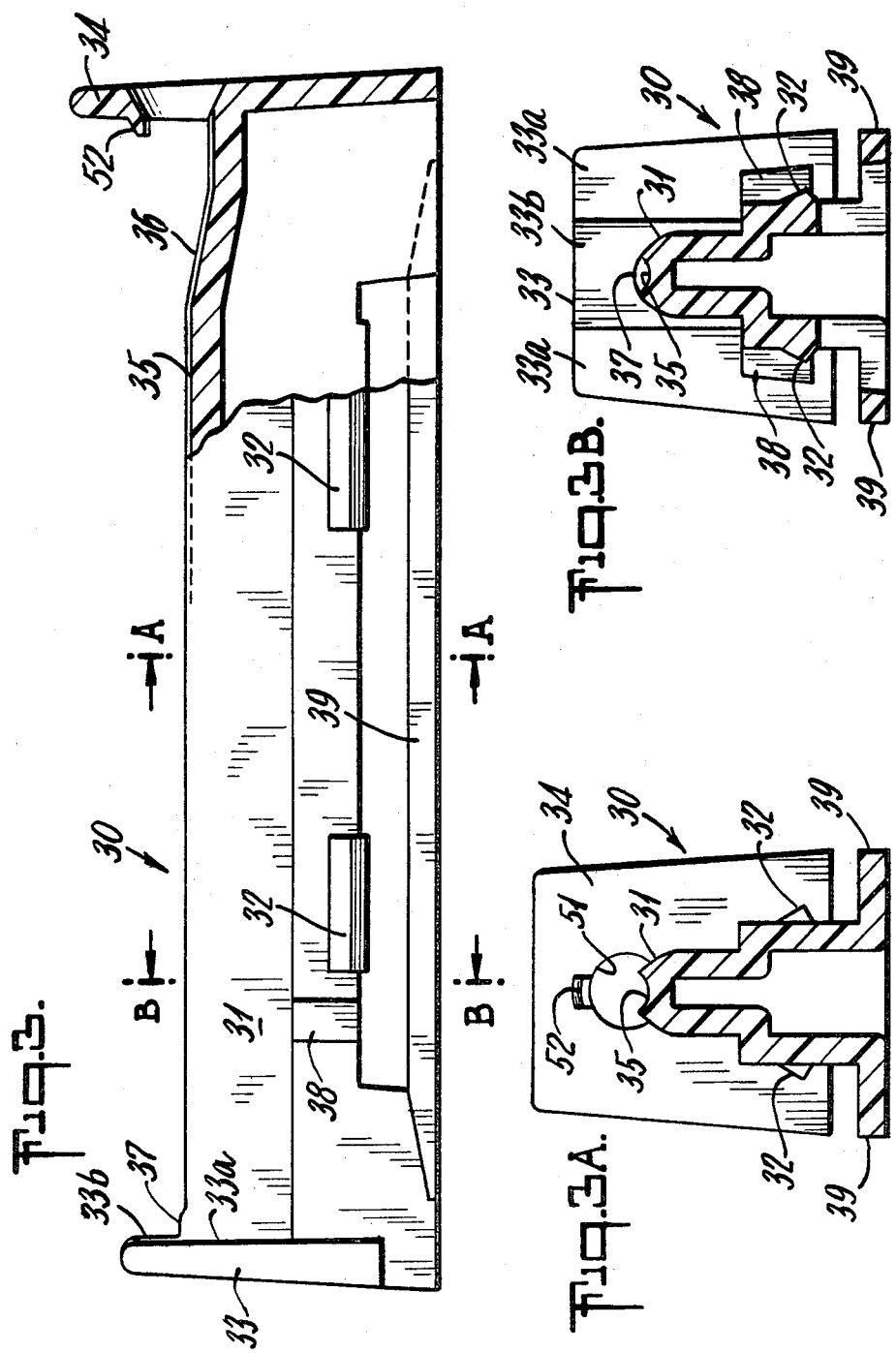

4,344,531

HEMOSTATIC CLIP CARTRIDGE

FIELD OF THE INVENTION

This invention relates to a hemostatic clip cartridge useful for holding hemostatic clips so that the clips are individually available to a hand held forceps-type clip applier when a surgeon requires such a hemostatic clip during the course of a surgical procedure.

BACKGROUND OF THE INVENTION

During surgical procedures it is necessary to occlude blood vessels, and while several means are available, the usual method is to clamp such vessels with hemostatic clips. Such clips are usually applied with a hand held forceps-type clip applier which deforms an open clip around the vessel to clamp it shut. See, for example, U.S. Pat. Nos. 3,326,216 and 3,363,628. Such appliers have specially shaped jaws into which individual clips are introduced and then applied to clamp a vessel. Various packaging means have been used in an effort to supply clips in a manner that is convenient to the surgeon and which involves a minimum of manipulation by the surgeon in picking up a clip in the applier so that it is firmly held until the surgeon has applied it to the particular vessel. Most clips are packaged in some form of cartridge which can be loaded and sterilized in a pouch. In general, the cartridges support individual clips in separate compartments. Such cartridges must provide some means of retaining the clips in place until picked up by the clip applier, and these retaining means often present difficulties or inconvenience to the surgeon who is using the clips.

BRIEF SUMMARY

This invention provides an improved hemostatic clip cartridge which automatically moves a plurality of pre-formed U-shaped hemostatic clips, which have been pre-loaded into the clip cartridge, to provide individual hemostatic clips serially at an open delivery station of the cartridge. The improved clip cartridge of this invention permits a surgeon to obtain an individual clip in a convenient manner from the same location each time a clip is needed without hindrance from the kind of retaining means associated with compartmented cartridges. In addition, the surgeon is not required to search for a compartment containing a clip, but knows that he can always obtain a clip from the single delivery station of the cartridge of the present invention.

The clip cartridge of this invention is formed of a base including a track on which the clips are moved, a cover which retains the clips which are not yet in position to be removed, and a slider which moves on the track and is spring-biased toward the delivery station and moves the contained clips along the track in that direction as each clip is removed. The delivery station of the cartridge is formed by the front end surface of the cover and the inside surface of the front end wall of the base. The delivery station is shaped so that the jaws of the clip applier will fit into the station in an attitude for picking up the clip positioned in the delivery station and so that the clip being picked up is supported against the pressure of the applier in engaging the clip.

BRIEF DESCRIPTION OF THE DRAWINGS

The clip cartridge of this invention will be described in more detail with reference to the accompanying drawings which show one illustrative specific embodiment of the invention.

In the drawings:

FIG. 2 is a side view of the clip cartridge assembly partly in section.

FIG. 2A is a rear end view of the clip cartridge assembly.

FIG. 3 is a side view of the base partly in section.

FIG. 3A is a section of the base taken along line A—A of FIG. 3.

FIG. 3B is a section of the base taken along line B—B of FIG. 3.

FIG. 4 is a side view of the cover partly in section.

FIG. 4A is a section of the cover taken along line A—A of FIG. 4.

DETAILED DESCRIPTION

Figure 1:
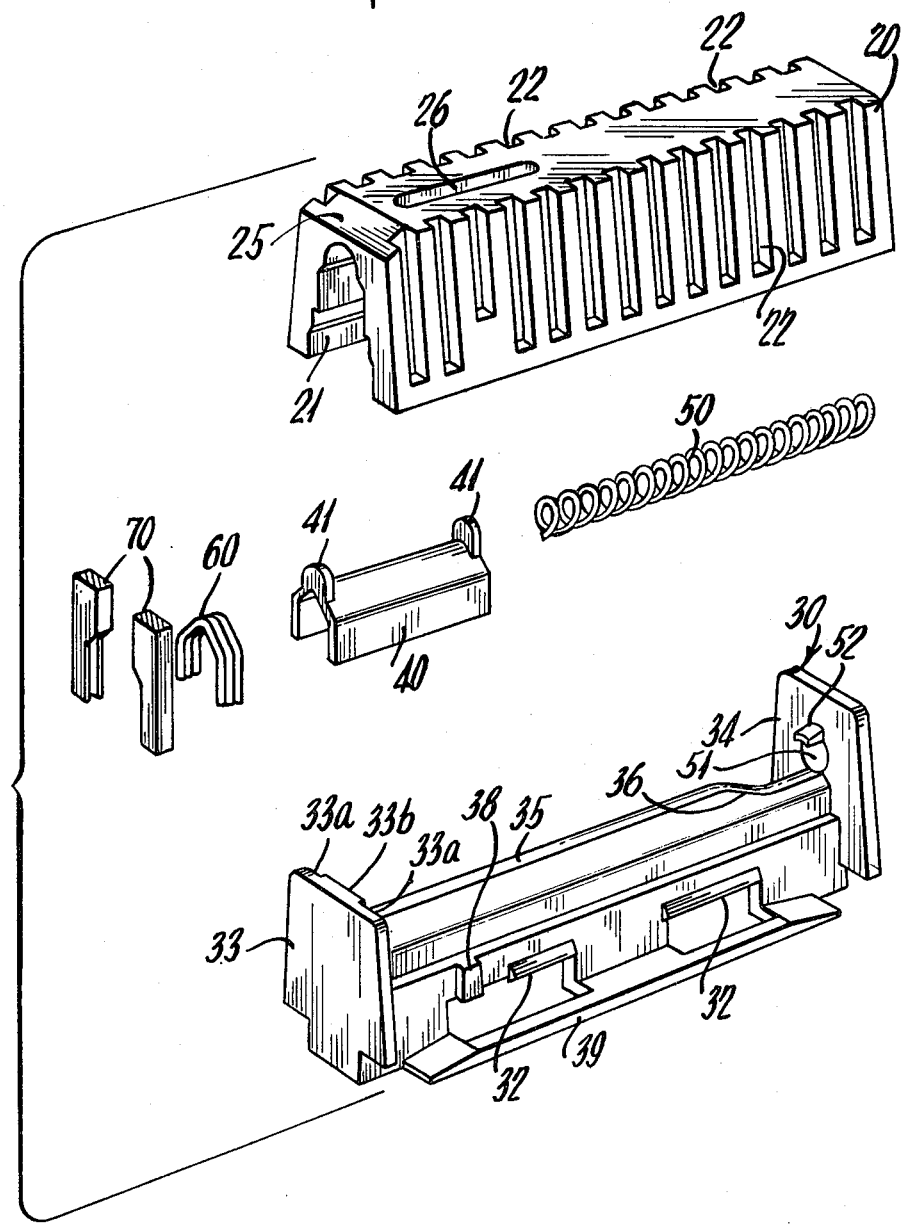
FIG. 1 is an isometric exploded view showing the parts of the clip cartridge in their relative positions to each other.

With reference to the accompanying drawings, identical parts are identified by the same reference numerals in all figures.

In FIG. 1, a specific embodiment of the clip cartridge of the present invention is shown with the individual parts separated but in their relative positions with respect to each other. The assembled cartridge is indicated generally by reference numeral 10 (in FIGS. 2 and 2A) and includes a cover 20, a base 30, a slider 40, and spring 50 as well as the contained hemostatic clips 60. The jaws only 70 of a forceps-type clip applier are shown in an attitude for picking up a clip.

The cover 20 is formed with its inside surface 21 contoured to fit on the base 30 and over track 31 with sufficient clearance from the track 31 to permit free passage of slider 40 and clips 60 but close enough to retain spring 50 as well as slider 40 and clips 60 in place no matter to what attitude the clip cartridge assembly 10 may be subjected between assembly and final use. The cover 20 may be formed with any outside surface but is preferably formed with a surface, such as channels 22, to facilitate gripping when the clip cartridge is hand held during use.

In order to position properly the cover 20 on the base 30, as will be explained hereinafter, the cover 20 is provided with two keyways 23 on opposite sides of the inside surface 21 of cover 20. The cover 20 is held to the base 30 by lugs 24 on the inside surface 21 of cover 20 which mate with lugs 32 on the outside of the base 30. As shown, four lugs are provided on both cover 20 and base 30. Obviously, other fastening means, adhesive as well as mechanical, may be used to fasten the cover 20 and base 30 together. Such means need not permit disassembly of the clip cartridge assembly 10 when, as will be the usual case, the clip cartridge assembly 10 is made to be disposable after the contained clips 60 are expended.

The cover 20 is preferably formed with a chamfer 25 at the top edge of the forward end of the cover 20 to provide easier access by the clip applier jaws 70 to the delivery station, which will be more fully described hereinafter.

The cover 20 is also preferably provided with a slot 26 in the forward part of the top surface of cover 20 to give visual access to the contained clips 60 to make it possible to ascertain the number of clips 60 remaining in the cartridge during use. To assist in such determination, the sides of slot 26 may be calibrated to show the number of clips 60 in the cartridge 10.

The base 30 includes track 31 which extends between the base end walls 33 and 34. The track 31 is provided with a groove 35 in its top edge to position and retain spring 50. A relieved portion 36 of track 31 at the rearward end thereof and up to base rear end wall 34 assists in assembly of spring 50, as will be explained hereinafter. The groove 35 stops before the track 31 meets the base forward end wall 33, and more precisely, by a distance of at least about the thickness of two contained clips 60 but no more than the length of the slider 40 so as not to interfer with the action of spring 50. This provides a step or platform 37 at the forward end of track 31 which is referred to herein as the delivery station. Such step or platform 37 may be raised slightly higher than the normal height of track 31, i.e., the height of track 31 before the shortening effect of groove 35. This platform 37 supports the clip 60 which is in the position to be removed by the clip applier jaws 70. Such support is necessary to prevent the clip 60 from being pushed by the clip applier jaws 70 to a position below the level of the following clip and binding against such following clip when the clip applier jaws 70 containing a clip 60 are being removed from the delivery station.

The base 30 has two keys 38, one on each side of the base 30, to mate with the keyways 23 in cover 20 during assembly to properly position the cover 20 on the base 30 and accurately fix the distance between inside surface of forward end wall 33 of the base 30 and the front surface of the forward end of cover 20 to precisely size the delivery station.

In order to make provision for the added width of clip applier jaws 70 as compared to the thickness of clips 60 and prevent the jamming of the jaws 70 in the delivery station, the inside surface of forward end wall 33 is relieved on each side to provide properly spaced bearing surfaces 33a for the jaws 70 and retain a properly positioned support surface 33b for the clip 60. The clip support surface 33b is closely dimensioned to the width of the contained clips 60.

Flanges 39 are provided on either side of the base 30 to make it possible to insert the clip cartridge assembly 10 in a holder when it is not to be hand held.

The slider 40 is shaped to fit on track 31 without binding or substantial friction as it is moved by spring 50. In cross-section, the slider 40 is substantially the shape of clips 60 so that it will be an effective pusher. Pads 41 provide a bearing surface for spring 50, and the slide 40 is shown with two pads 41 to make it completely symetrical for ease of assembly.

In assembling the clip cartridge 10, the clips 60 and slider 40 are placed on track 31 and cover 20 fastened to base 30 with the aid of keys 38 and keyways 23 to position the cover 20 and mating lugs 24 and 32. The spring 50 is then inserted through the spring assembly hole 51 which is possible because of the relieved portion 36 of track 31. The spring 50 climbs the inclined portion 36 of track 31 and, guided by groove 35, contacts the pad 41 of slider 40. When compressed into the interior of clip cartridge 10, the spring 50 will be supported by the flat portion of track 31. When released the spring 50 no longer will be aligned with hole 51 but will surround retention stud 52 and be retained within clip cartridge 10 to provide the biasing of slider 40. Other biasing means may be used in place of spring 50 and associated structures.

The clip cartridge of the present invention has the many advantages noted previously. In addition, because it delivers clips from a single delivery station, two of the present clip cartridges can be placed "nose to nose" in a cartridge holder to supply two clips simultaneously to a double-time clip applier. When the two sets of jaws of the doubletime clip applier are first inserted into the two cartridges, the jaws will properly position the two cartridges in the holder to make available two clips at a time to that double-time applier.

The clip cartridge of this invention has been described in connection with pre-formed U-shaped hemostatic clips, but it is obvious that this clip cartridge could be used for other clips of a different configuration by modifying the shape of the inside surface of the cover, the shape of the track and slider, and the shape of the delivery station.

What is claimed is:

1. A clip cartridge adapted to contain hemostatic clips in serial arrangement comprising a cover, a base including a track connecting front and rear end walls of said base, said track shaped to accommodate said clips in serial arrangement thereon and permit said clips to be moved along said track toward the front end wall of said base, a slider shaped to fit on said track and adapted to move along said track, and means to bias said slider toward the front end wall of said base; said cover having an inside surface contoured to fit on said base and over said track to enclose said track for a major part of track length in a manner retaining said clips and said slider on said track while permitting said clips and said slider to move on said track, said cover being positioned on said base to provide a delivery station at an unenclosed portion of said track between outside surface of forward end of said cover and inside surface of front end wall of said base to permit removal of individual clips from said cartridge by a separate retrevial device.

2. A clip cartridge according to claim 1, which contains a plurality of pre-formed U-shaped hemostatic clips located on said track between the front end wall of said base and said slider, and said delivery station is sized to provide individual clips serially to a separate retrevial device.

3. A clip cartridge according to claim 1, including a platform at forward end of said track extending rearwardly from the front end wall of said base a distance no greater than the length of said slider.

4. A clip cartridge according to claim 1, wherein the means to bias said slider includes a spring, a spring-retention stud on inside surface of said cover, a spring-retention groove in top of said track, and a spring bearing surface on said slider.

* * * * *